(12) United States Patent
Song

(10) Patent No.: US 8,758,246 B2
(45) Date of Patent: Jun. 24, 2014

(54) ULTRASOUND SYSTEM WITH CONTROL PANEL ADJUSTABLE IN HEIGHT THROUGH CONTACT

(75) Inventor: Jung Sik Song, Seoul (KR)

(73) Assignee: Samsung Medison Co., Ltd., Hongcheon-Gun, Gangwon-Gu (KR)

( * ) Notice: Subject to any disclaimer, the term of this patent is extended or adjusted under 35 U.S.C. 154(b) by 207 days.

(21) Appl. No.: 12/574,985

(22) Filed: Oct. 7, 2009

(65) Prior Publication Data

US 2010/0087734 A1    Apr. 8, 2010

(30) Foreign Application Priority Data

Oct. 8, 2008  (KR) .................. 10-2008-0098576

(51) Int. Cl.
*A61B 8/00* (2006.01)

(52) U.S. Cl.
USPC ........... 600/437; 600/407; 600/441; 600/447; 600/439

(58) Field of Classification Search
USPC .......................... 600/407, 437, 441, 447, 439
See application file for complete search history.

(56) References Cited

U.S. PATENT DOCUMENTS

| | | | |
|---|---|---|---|
| 5,415,169 A * | 5/1995 | Siczek et al. ................. 600/427 |
| 5,664,573 A * | 9/1997 | Shmulewitz ................. 600/445 |
| 6,663,569 B1 * | 12/2003 | Wilkins et al. ............... 600/459 |
| 7,736,312 B2 * | 6/2010 | Taylor et al. ................. 600/437 |
| 2003/0220564 A1 * | 11/2003 | Wilkins et al. ............... 600/437 |
| 2008/0161688 A1 * | 7/2008 | Poland ......................... 600/437 |
| 2009/0177083 A1 * | 7/2009 | Matsumura ................... 600/437 |

FOREIGN PATENT DOCUMENTS

| | | |
|---|---|---|
| JP | 2005-198916 A | 7/2005 |
| JP | 2005-526566 A | 9/2005 |
| JP | 2008-067794 A | 3/2008 |

OTHER PUBLICATIONS

Japanese Office Action issued in Japanese Application No. 2009-230810 dated Nov. 19, 2013.

* cited by examiner

*Primary Examiner* — Unsu Jung
*Assistant Examiner* — Joel Lamprecht
(74) *Attorney, Agent, or Firm* — McDermott Will & Emery LLP

(57) ABSTRACT

Disclosed herein is an ultrasound system which has a control panel adjustable in height. The ultrasound system includes the control panel, a power transmission device adjusting a height of the control panel, a contact detection unit detecting contact and generating a selection signal, and a controller controlling the power transmission device according to the selection signal.

7 Claims, 3 Drawing Sheets

ULTRASOUND SYSTEM WITH CONTROL PANEL ADJUSTABLE IN HEIGHT THROUGH CONTACT

CROSS-REFERENCE TO RELATED APPLICATIONS

This application claims the benefit of Korean Patent Application No. 10-2008-0098576, filed Oct. 8, 2008, the entire contents of which are incorporated by reference herein.

BACKGROUND OF THE INVENTION

1. Field of the Invention

The present invention relates to an ultrasound system and, more particularly, to an ultrasound system that allows a user to adjust the height of a control panel with a contact detection unit detecting contact of the user and a power transmission device capable of performing a brake operation with electric power.

2. Description of the Related Art

Generally, an ultrasound system refers to a non-invasive apparatus that irradiates an ultrasound signal from a surface of a patient body towards a target internal organ within the body surface and obtains an image of a monolayer or blood flow in soft tissue from information in the reflected ultrasound signal (ultrasound echo-signal). The ultrasound system has been widely used for diagnosis of the heart, the abdomen, the urinary organs, and in obstetrics and gynecology due to its various merits such as a small size, a low price, real-time image display, and high stability through elimination of any radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

Particularly, a conventional ultrasound system includes a control panel, through which a user can select measurement modes and functions, and optimize an ultrasound image displayed on a screen of a display unit. The control panel includes a touch screen which displays menus for optimizing an ultrasound image displayed on the screen of the display unit and provides a function of selecting the menus displayed thereon, a track ball which is used to move a cursor displayed on the screen of the display unit and provides a function of searching images from Cine-images, a keyboard which is used to input text and provides short cuts according to the measurement modes, and the like.

Here, it should be noted that the above description is not given for illustration of a conventional technique to which the present invention pertains, but for understanding of the background of the present invention.

A conventional ultrasound system includes a mechanical manipulating device such as a lever to adjust the height of the control panel. With this configuration, when a user adjusts the height of the control panel during ultrasound diagnosis, the conventional ultrasound system requires the user to halt diagnosis and manually adjust the height of the control panel with the lever, thereby providing inconvenience to the user. Therefore, there is a need for an improved ultrasound system that overcomes such a problem.

SUMMARY OF THE INVENTION

The present invention is conceived to solve the problem of the conventional technique as described above, and an aspect of the present invention is to provide an ultrasound system that allows a user to adjust the height of a control panel using a contact detection unit detecting contact of the user and a power transmission device capable of performing a brake operation with electric power, thereby improving user convenience in ultrasound diagnosis with the ultrasound system.

According to an aspect of the present invention, an ultrasound system having a control panel adjustable in height through contact is provided. The ultrasound system includes the control panel; a power transmission device adjusting a height of the control panel; a contact detection unit detecting contact and generating a selection signal; and a controller controlling the power transmission device according to the selection signal.

The contact detection unit may be mounted on a handle of the control panel.

The contact detection unit may include a light emitting diode (LED) which displays a contact state of a user with the contact detection unit.

The contact detection unit may include at least one of a pressure sensor, an electrostatic capacity sensor, and a temperature sensor.

The selection signal may be classified according to a contact period of time with the contact detection unit.

The power transmission device may include a brake driven by electric power.

The ultrasound system may further include an operation display unit displaying an operating state of the power transmission device according to an output from the controller.

The operation display unit may include at least one of an LED, a speaker, and a display.

As apparent from the above description, the ultrasound system according to an embodiment of the present invention allows a user to adjust the height of the control panel using the contact detection unit detecting contact of the user and the power transmission device capable of performing a brake operation with electric power, thereby improving user convenience in ultrasound diagnosis with the ultrasound system.

Further, the ultrasound system according to another embodiment of the present invention allows a user to more easily check and determine an operating state and an operation start time of the power transmission device through the operation display unit, so that the user can adjust the height of the control panel more conveniently.

BRIEF DESCRIPTION OF THE DRAWINGS

The above and other aspects, features and advantages of the present invention will become apparent from the following description of exemplary embodiments given in conjunction with the accompanying drawings, in which.

DETAILED DESCRIPTION OF THE EMBODIMENT

Exemplary embodiments of the present invention will now be described in detail with reference to the accompanying drawings hereinafter. It should be noted that the drawings are not to precise scale and may be exaggerated in thickness of lines or size of components for descriptive convenience and clarity only. Furthermore, terms used herein are defined by taking functions of the present invention into account and can be changed according to the custom or intention of users or operators. Therefore, definition of the terms should be made according to overall disclosures set forth herein.

Figure 1:
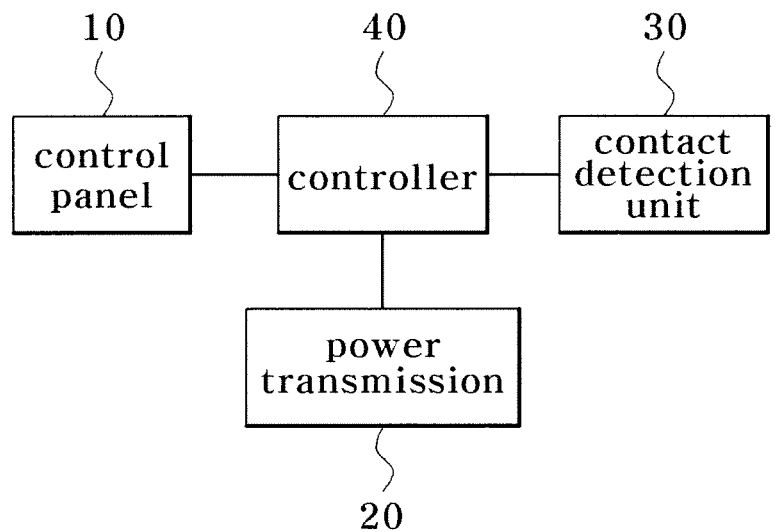
FIG. 1 is a block diagram of an ultrasound system according to an exemplary embodiment of the present invention.

FIG. 1 is a block diagram of an ultrasound system according to an exemplary embodiment of the present invention.

As shown in FIG. 1, the ultrasound system according to the embodiment of the invention includes a control panel 10, a power transmission device 20, a contact detection unit 30, and a controller 40.

Operation of the ultrasound system with the control panel adjustable in height through contact according to the embodiment of the invention will be described in detail.

When a user holds the contact detection unit 30 to adjust the height of the control panel 10 during ultrasound diagnosis with the ultrasound system, the contact detection unit 30 detects contact of the user and generates a selection signal.

Here, the contact detection unit 30 includes at least one of a pressure sensor, an electrostatic capacity sensor and a temperature sensor, and generates the selection signal after detecting the contact of the user via the respective sensors.

The selection signal may be classified according to a contact period of time of the user. For example, when the user holds the contact detection unit 30 for a predetermined period of time or more, the contact detection unit 30 may generate a selection signal which instructs operation of the power transmission device 20. The predetermined period of time may be 1 or 2 seconds.

When the selection signal is generated, the controller 40 receives the selection signal and controls the power transmission device 20 in response to the selection signal. Then, the power transmission device 20 adjusts the height of the control panel 10 according to the control of the control panel 40.

The power transmission device 20 may include a brake driven by electric power. For example, the power transmission device 20 includes an electric brake which can be turned-on/off by electric power, so that, when a user holds the contact detection unit 30 for a predetermined period of time or more, the power transmission device 20 releases the brake according to the control of the controller 40 to allow the user to adjust the height of the control panel 10. When the user stops contacting the contact detection unit 30, the power transmission device 20 operates the brake according to the control of the controller 40 to allow the control panel 10 to be secured at a desired height.

According to one embodiment of the invention, the contact detection unit 30 may be mounted on a handle of the control panel 10 and may include an LED to display a contact state between a user and the contact detection unit 30.

Figure 2:
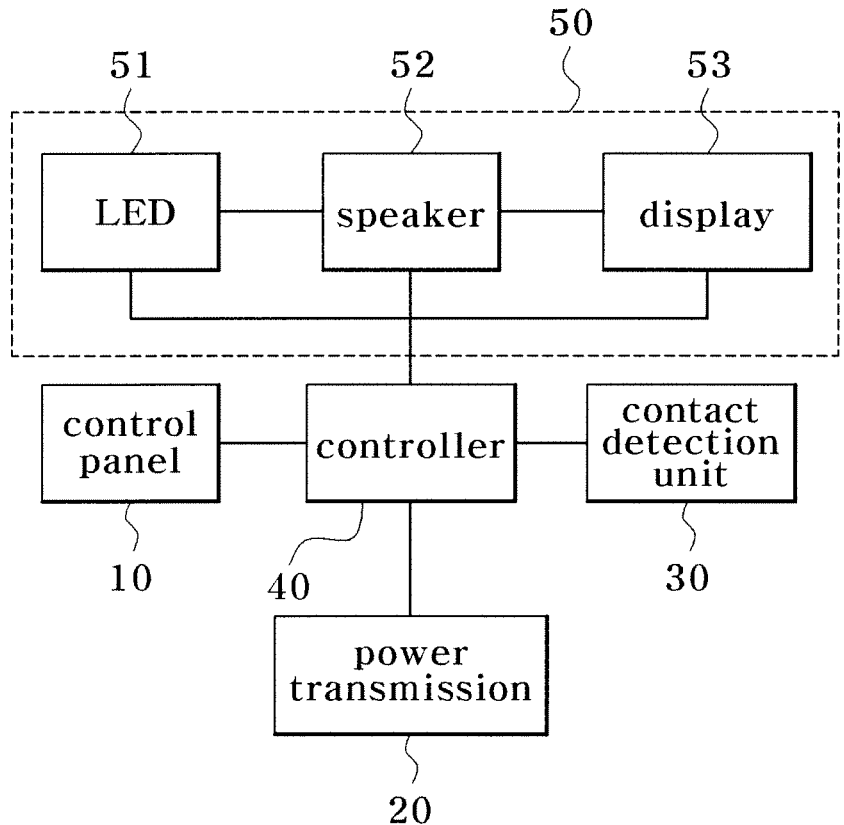
FIG. 2 is a block diagram of an ultrasound system including an operation display unit according to an exemplary embodiment of the present invention.

FIG. 2 is a block diagram of an ultrasound system including an operation display unit according to an exemplary embodiment of the present invention.

Operation of the ultrasound system including the operation display unit 50 will be described in detail with reference to FIG. 2. As described above, the controller 40 receives a selection signal and controls the power transmission device 20 according to the received selection signal.

When the controller 40 outputs a control signal, the operation display unit 50 displays an operation state of the power transmission device 20 according to the control signal output from the controller 40.

The operation display unit 50 may include at least one of an LED 51, a speaker 52, and a display 53.

For example, if the LED 51 is used, the LED 51 emits blue light when a user contacts the contact detection unit 30 for a predetermined period of time or more to release the brake of the power transmission device 20, and emits red light when the user stop contacting the contact detection unit 30 to operate the brake of the power transmission device 20.

Similarly, if the speaker 52 is used, the speaker 52 generates a long beep sound and a short beep sound according to an output from the controller 40 when the brake of the power transmission device 20 is released and operated, respectively, thereby allowing the user to easily recognize the operation state of the power transmission device 20.

Further, if the display 53 is used, the display 53 displays associated words, figures or the like according to an output from the controller 40 when the brake of the power transmission device 20 is released and operated, respectively.

When one or more of the LED 51, the speaker 52 and the display 53 are used not individually but cooperatively, a user can more easily recognize the operation state of the power transmission device 20.

Figure 3:
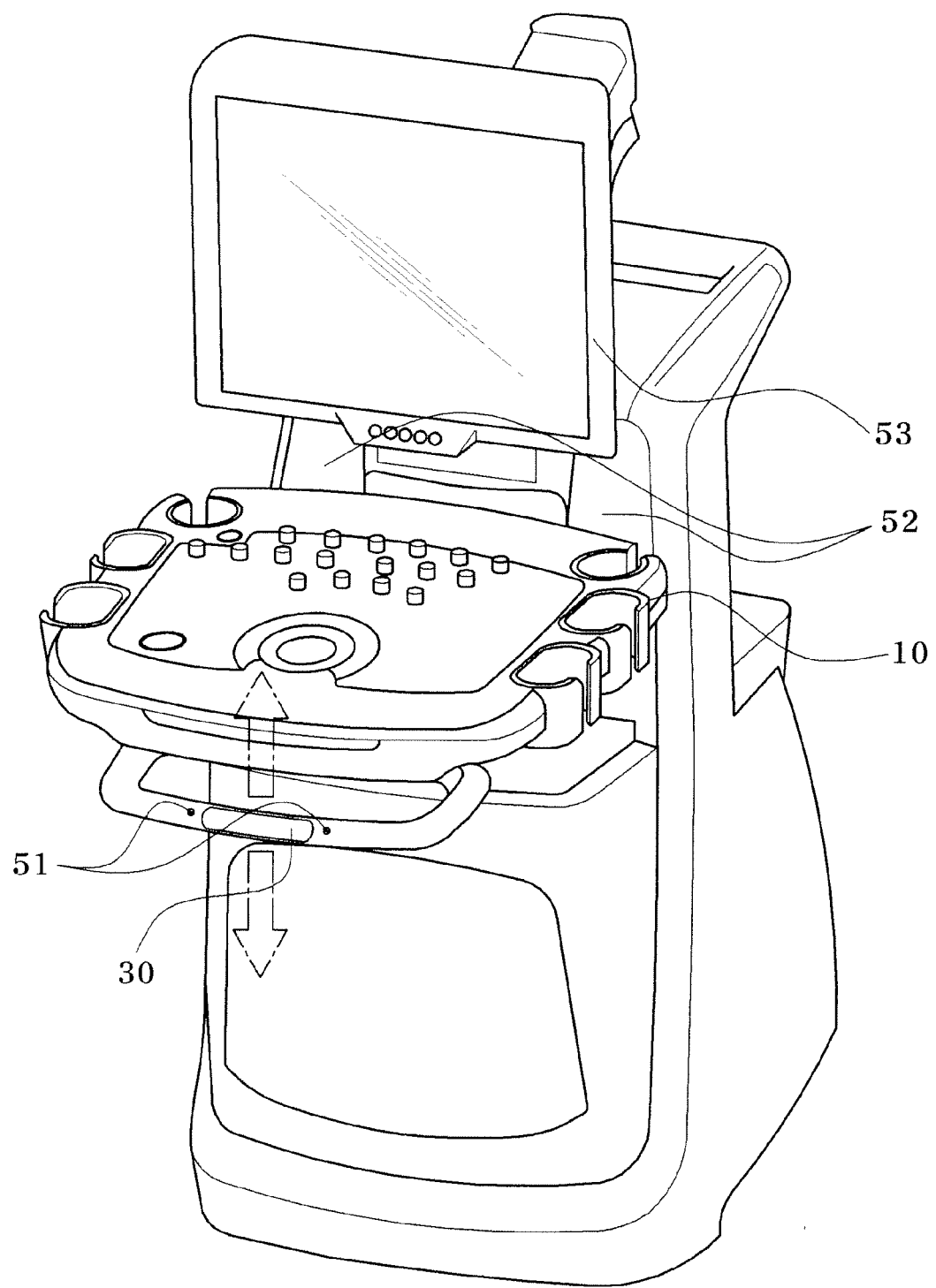
FIG. 3 is a perspective view of an ultrasound system with a control panel adjustable in height through contact according to an exemplary embodiment of the present invention.

FIG. 3 is a perspective view of an ultrasound system with a control panel adjustable in height through contact according to an exemplary embodiment of the present invention.

As shown in FIG. 3, a user can adjust the height of the control panel 10 by touching the contact detection unit 30 mounted on the handle of the control panel 10, as described above. The user can easily recognize an operation state of the power transmission device 20 through the LED 51, the speaker 52 or the display 53 which constitutes the operation display unit 50.

Figure 4:
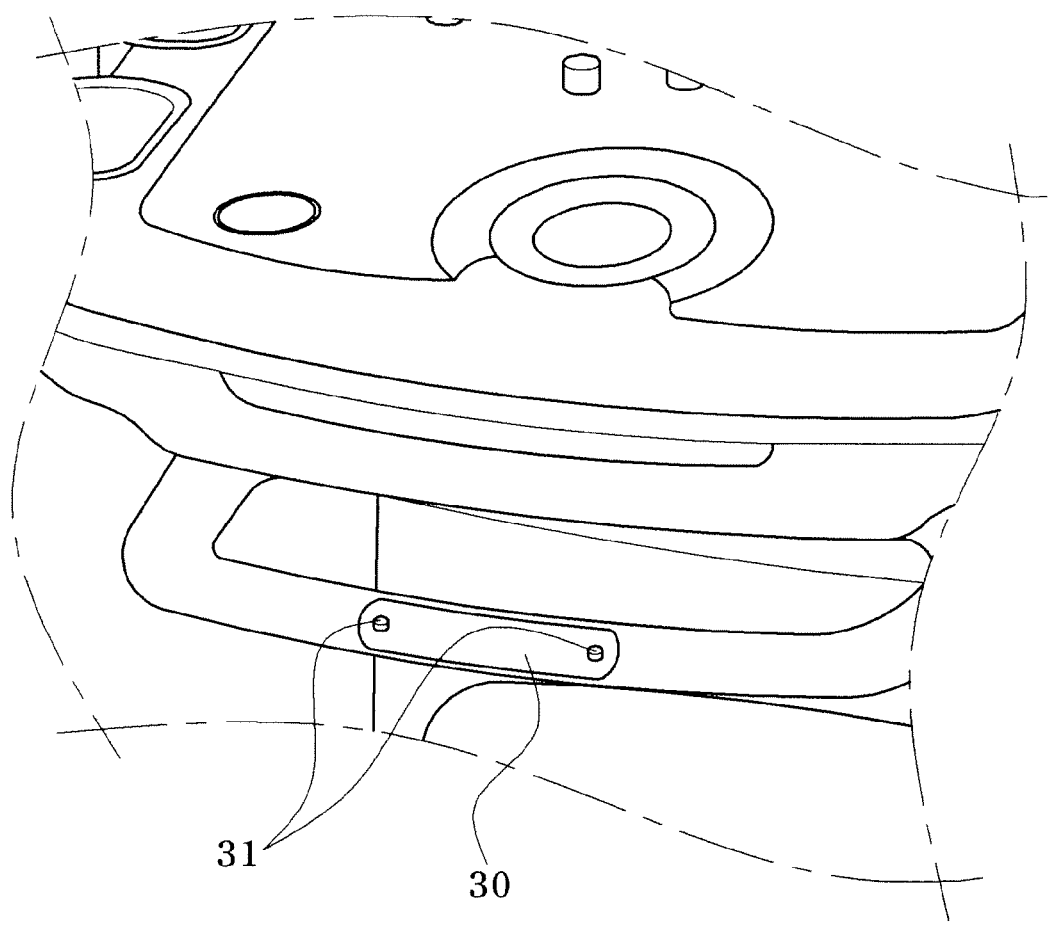
FIG. 4 shows a contact detection unit according to an exemplary embodiment of the present invention.

FIG. 4 shows a contact detection unit according to an exemplary embodiment of the present invention.

As shown in FIG. 4, the contact detection unit 30 may include an LED 31, on which a contact state between a user and the contact detection unit 30 can be displayed. For example, the LED 31 emits yellow light while the user contacts the contact detection unit 30, and emits red-orange light when the user stops contacting the contact detection unit 30, thereby making it easy for the user to judge whether the contact between the user and the contact detection unit 30 is sufficiently carried out.

As such, the ultrasound system according to one embodiment of the present invention allows a user to adjust the height of a control panel using a contact detection unit detecting contact of the user and a power transmission device capable of performing a brake operation with electric power, thereby improving user convenience in ultrasound diagnosis with the ultrasound system.

Further, the ultrasound system according to another embodiment of the present invention allows a user to more easily check and determine an operating state and an operation start time of the power transmission device through an operation display unit, so that the user can adjust the height of the control panel more conveniently.

Although the present invention has been described with reference to the embodiments, it will be apparent to those skilled in the art that the embodiments are given by way of illustration only, and that various modifications and equivalent embodiments can be made without departing from the spirit and scope of the present invention. Accordingly, the scope of the present invention should be limited only by the accompanying claims.

What is claimed is:

1. An ultrasound diagnostic system for irradiating an ultrasound signal towards a patient and having a control panel adjustable in height through contact, the ultrasound system comprising:

the control panel;
a power transmission device configured to adjust a height of the control panel;
a contact detection unit configured to detect contact, and generate a selection signal when the contact detection unit detects holding of the contact detection unit by a user for a predetermined period of time or more; and
a controller configured to control the power transmission device according to the selection signal,
wherein the contact detection unit is mounted on a handle of the control panel and has an area of a predetermined size and includes at least one of a pressure sensor, an electrostatic capacity sensor and a temperature sensor.

2. The ultrasound diagnostic system according to claim 1, wherein the contact detection unit comprises a light emitting diode (LED) configured to display a contact state of a user with the contact detection unit.

3. The ultrasound diagnostic system according to claim 1, wherein the-power transmission device comprises a brake driven by electric power, and
wherein the power transmission device is configured to release the brake to allow the user to adjust the height of the control panel when the user holds the contact detection unit for the predetermined period of time or more.

4. The ultrasound diagnostic system according to claim 1, wherein the power transmission device comprises a brake driven by electric power, and
wherein the power transmission device is configured to operate the brake to allow the control panel to be secured at a desired height when the user stops contacting the contact detection unit.

5. The ultrasound diagnostic system according to claim 1, further comprising:
an operation display unit configured to display an operating state of the power transmission device according to an output from the controller.

6. The ultrasound diagnostic system according to claim 5, wherein the operation display unit is at least one of an LED, a speaker, and a display.

7. The ultrasound diagnostic system according to claim 1, wherein the contact detection unit is arranged to move in accordance with movement of the control panel when the height of the control panel is being adjusted.

* * * * *